United States Patent [19]

Payne, Jr. et al.

[11] Patent Number: 5,356,948
[45] Date of Patent: Oct. 18, 1994

[54] LUBRICIOUS RADIATION STABLE POLYMERIC COMPOSITION AND METHOD FOR STERILIZING THEREFROM

[75] Inventors: Donald N. Payne, Jr., Durham, N.C.; Jess M. Waller, Akron, Ohio; Richard P. Clarke, Raleigh, N.C.; George R. Titus, Raleigh, N.C.; David A. Martin, Raleigh, N.C.

[73] Assignee: Becton, Dickinson and Company, Franklin Lakes, N.J.

[21] Appl. No.: 186,488

[22] Filed: Jan. 26, 1994

Related U.S. Application Data

[62] Division of Ser. No. 576,750, Sep. 4, 1990.

[51] Int. Cl.$^5$ .............................. C08J 3/28; C08J 5/16; C08K 5/20
[52] U.S. Cl. .............................. 522/75; 522/74; 522/78; 522/79; 522/155; 522/156; 522/157; 522/161
[58] Field of Search .............. 522/74, 78, 79, 157, 522/161, 155, 156, 75

[56] References Cited

U.S. PATENT DOCUMENTS

| | | | |
|---|---|---|---|
| 4,70,116 | 7/1988 | Roberts | 525/221 |
| 3,645,822 | 2/1972 | Widiger et al. | 156/243 |
| 4,016,118 | 4/1977 | Hamada et al. | 260/17.45 G |
| 4,110,185 | 8/1978 | Williams et al. | 204/159.2 |
| 4,274,932 | 6/1981 | Williams et al. | 204/159.2 |
| 4,371,645 | 2/1983 | Mahaffey, Jr. | 524/108 |
| 4,394,474 | 7/1983 | McKinney et al. | 524/232 |
| 4,430,289 | 2/1984 | McKinney et al. | 264/564 |
| 4,454,272 | 6/1984 | McKinney et al. | 524/241 |
| 4,529,764 | 7/1985 | McKinney et al. | 524/232 |
| 4,534,799 | 8/1985 | Aguirre | 106/270 |
| 4,563,259 | 1/1986 | Rayner | 524/99 |
| 4,694,026 | 9/1987 | Park | 521/94 |
| 4,767,414 | 8/1988 | Williams et al. | 604/230 |
| 4,785,034 | 11/1988 | Gaku et al. | 524/99 |
| 4,845,137 | 7/1989 | Williams et al. | 524/108 |

Primary Examiner—Susan W. Berman
Attorney, Agent, or Firm—Richard E. Brown

[57] ABSTRACT

A lubricious polymeric composition which is stable toward sterilizing radiation includes a semicrystalline polyolefin of narrow molecular weight distribution having incorporated therein a liquid mobilizing additive, a radiation stabilizing amount of a hindered amine, a lubricating amount of an erucic acid derivative and a clarifying amount of a sorbitol derivative. The invention includes a sterilized article fabricated from the composition and a method to radiation sterilize the article.

3 Claims, 3 Drawing Sheets

LUBRICIOUS RADIATION STABLE POLYMERIC COMPOSITION AND METHOD FOR STERILIZING THEREFROM

This is a division of application Ser. No. 07/576,750, filed Sep. 4, 1990.

BACKGROUND OF THE INVENTION

1. Field of the Invention

The present invention relates to polymeric articles and more particularly relates to lubricious polymeric articles which retain their lubricity during application of sterilizing radiation.

2. Background of the Invention

Semicrystalline polymeric materials, including the polyolefins of which polypropylene is most significant with respect to the present invention, are often employed in producing shaped articles subsequently subjected to irradiation sterilization techniques. For example, in the health and medical field, these sterilizable articles include syringes, tubing and tube assemblies, microbiological plastics, flasks, package film and the like. It is well-known that these semicrystalline polymeric materials, if not properly stabilized, will discolor and become embrittled as a result of sterilization by exposure to high energy radiation at levels above 0.1 megarads.

Further, after irradiation has been completed, post irradiative oxidation continues due to free radicals generated by the irradiation which participate in branching chain reactions. Therefore, while degradation of the mechanical properties of these polymeric materials may not be obvious immediately after irradiation, they become more pronounced as time goes on. Thus, much effort has been expended toward agents or additives which would stabilize polymeric materials toward post irradiation degradation.

Some recent attempts have been made to improve the stability of semicrystalline polymeric materials as to reduce embrittlement. Williams et al. U.S. Pat. No. 4,110,185 discloses flexible sterilized articles comprising a semicrystalline polymer having a noncrystalline mobilizing additive incorporated therein. The additive increases the free volume of the polymer which is believed to account for the improved stability during and subsequent to irradiation.

In Williams et al. U.S. Pat. No. 4,274,932, a further improvement in radiation stability is achieved by including the above mobilizing additive in a semi crystalline polymer having a narrow molecular weight distribution.

Polyolefins containing a sterically hindered amine stabilizing agent are disclosed in Gaku et al. U.S. Pat. No. 4,785,034 in Rayner U.S. Pat. No. 4,563,259 and in Japanese Patent J60099-147-A.

In addition to a requirement for radiation stability, some articles also require a lubricious surface. Roberts U.S. Pat. No. 4,760,116 discloses films of crosslinked polyethylene compositions containing fatty acid amide slip agents to provide a satisfactory coefficient of friction (COF).

Articles requiring both sterilization and lubricity at a surface to surface interface, such as a syringe barrel and plunger, present a different problem. Application of a conventional lubricant, such as a hydrocarbon oil or a silicone oil, to the interface has not been satisfactory because many of these lubricants are subject to air oxidation resulting in viscosity changes, objectionable color development, and a tendency to migrate and form beads. For medical articles to be sterilized after packaging, degradation of the lubricant during sterilization or during shelf life may compromise the performance of the article. An approach to overcoming this problem is plasma treatment as disclosed in Williams et al. U.S. Pat. No. 4,767,414.

In some applications, polymeric materials are used in forms such as plates, sheets, films and the like in which clarity or transparency is a very desirable property. Clarity may also be important for certain plastic articles, such as syringes, made by injection molding. Additives which improve clarity have been disclosed by Hamada et al. in Mahaffey et al. U.S. Pat. No. 4,016,118 in Williams et al. U.S. Pat. No. 4,371,645 and in U.S. Pat. No. 4,845,137.

In copending application Ser. No. 362,999, now U.S. Pat. No. 4,959,402 of common assignee herewith, there is disclosed a polyolefin composition of high clarity and stability to radiation sterilization provided by combining the polyolefin with a mobilizing oil, a dibenzylidene sorbitol clarifier and a hindered piperidine stabilizer.

There is a need, unaddressed hitherto in the art, for a lubricious polyolefin composition capable of slidable face-to-face movement over a second surface in an article which can be radiation sterilized after packaging without discoloration, loss of mechanical properties or loss of lubricity. It is toward fulfillment of this need that the present invention is directed.

SUMMARY OF THE INVENTION

One aspect of the present invention is a lubricious polymeric composition which may be radiation sterilized without degradation due to the radiation. The composition includes a polyolefin having a narrow molecular weight distribution, a liquid mobilizing additive miscible with the polyolefin which increases the free volume of the polyolefin, a radiation stabilizing amount of a hindered amine and a lubricating amount of an erucic acid derivative. Preferred compositions also include a dibenzylidene sorbitol clarifying agent.

The polyolefin may be a homopolymer or a copolymer of preferably polypropylene having a ratio of the weight average molecular weight to the number average molecular weight of no greater than 9, preferably about 2 to 4. The preferred mobilizer has a density of about 0.6 to 1.9 and most preferably is a hydrocarbon oil or a phthalic ester. The preferred stabilizer is a hindered piperidine ester of a dicarboxylic acid, the preferred clarifier is a dibenzylidene sorbitol and the preferred lubricant is erucyl erucamide.

A second aspect of the invention is an article, preferably a sterilized medical article fabricated from the composition of the invention. Preferred sterilized articles are tube assemblies and syringes, most preferably two-piece syringes.

The invention includes a method for preparing a sterilized composition or article by subjecting the composition or article to a sterilizing dose of high energy radiation, preferably from a cobalt-60 source.

In accordance with the principles of the present invention, lubricious polyolefinic compositions, and particularly, polypropylene compositions, are sterilizable and rendered stable to high energy irradiation without loss of lubricity. The combination of a hindered piperidine and a liquid mobilizer provides a level of stabilization that the individual materials, acting alone, would not normally impart to polymeric material subjected to high doses of radiation. Post irradiative oxidative degradation is substantially reduced so that the mechanical properties of the polymer are not compromised. At the same time, the preferred combinations of polymer and radiation stabilizing additives not only show good resistance to post-irradiative oxidation but also resist discoloration while retaining flexibility. The erucyl lubricant migrates slowly to the surface of the composition and may thus be compounded in the composition before molding. The molded parts may then be assembled, packaged and the sealed package irradiation sterilized, preferably after a lubricating quantity of the erucyl derivative has migrated to the surface. No substantial loss in lubrication occurs during extended shelf time so that the article is lubricious when used and is not limited to use during a dated period. These features are highly advantageous, particularly when the improved compositions are fabricated into articles such as syringes and other medical products which require sterilization and lubricity at a surface to surface interface.

DETAILED DESCRIPTION

Figure 1:
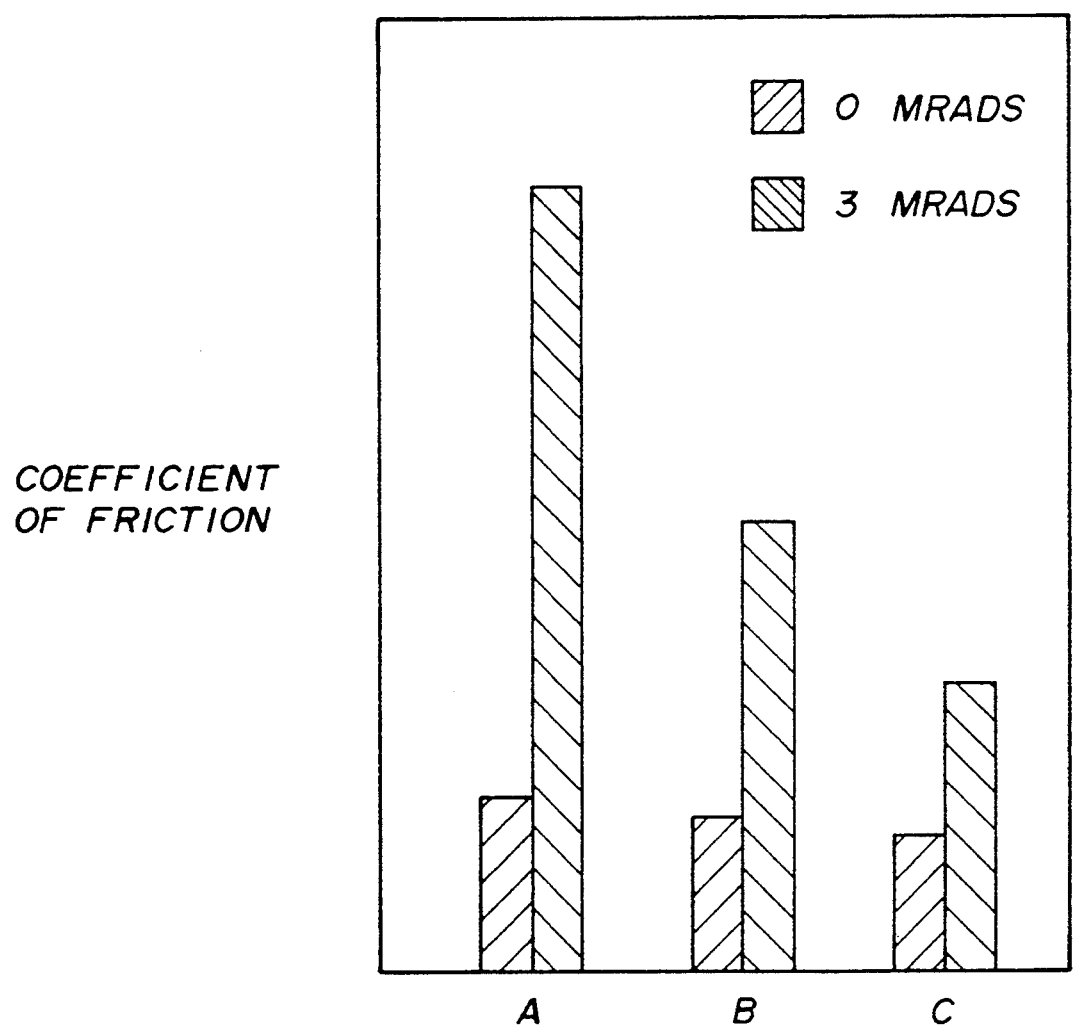
FIG. 1 illustrates the COF, before and after radiation sterilization, of polypropylene compositions of the invention compared a similar composition lubricated with a conventional lubricant.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The polyolefin of the present invention may be described as basically linear, but may optionally contain side chains such as are found, for instance, in conventional, low density polyethylene. It may be a homopolymer or a copolymer of an aliphatic monoolefin, preferably having about 2 to 6 carbon atoms. Exemplary of such polyolefins are polyethylene, polymethylpentene, polytetrafluoroethylene and the like. The preferred polyolefin is polypropylene.

The polyolefin may contain a small amount, generally from about 0.1 to 10 percent of an additional polymer incorporated into the composition by copolymerization with the appropriate monomer. Such copolymers may be added to the composition to enhance other characteristics of the final composition, and may be, for example, polyacrylate, polyvinyl, polystyrene and the like.

It is preferred that the polyolefin of the composition be of narrow molecular weight distribution. The molecular weight distribution of a polymer is defined by the ratio of the weight average molecular weight (Mw) and the number average molecular weight (Mn) wherein the minimum possible ratio of 1.0 defines the polymer having all the chains the same size. Suitable polyolefins for the composition of the invention may have a number average molecular weight of about 10,000 to 400,000, preferably 30,000 to 50,000 and a ratio of from 1 to 9 preferably about 2 to 6, as determined by conventional gel permeation chromatography. Most preferably the ratio is about 2 to 4.

In addition to being of narrow molecular weight distribution, the polyolefin of the invention is preferably semicrystalline. Preferred polyolefins have a crystalline content of about 20 to 90, preferably about 40 to 80, most preferably about 45 to 65%. The degree of crystallinity is linearly proportional to the density of the sample and, as known in the art, may be measured with a conventional density gradient column.

The composition of the invention may include one or more additives which contribute to radiation stability and at least one radiation stable lubricating additive. The first stabilizing additive is a mobilizing additive of the type described in the aforementioned U.S. Pat. No. 4,274,932. The mobilizer may be a low molecular weight noncrystalline substance which is miscible with the polymeric material and is also compatible therewith, i.e., the mobilizer does not adversely affect the properties of the polymer. The mobilizer may be a substance which increases the free volume of the polymer and, therefore, also lowers the density of the polymer. The mobilizer functions to mobilize the amorphous portion of the polymer, and as a result, increases the radical termination reactions which prevent or minimize degradation during and subsequent to the irradiation.

A wide variety of liquids which increase the total free volume of the polymer may serve as the mobilizer. The term liquid as used herein includes highly viscous substances, commonly referred to as greases. In general, such mobilizers have a density of from 0.6 to 1.9 $g/cm^3$, and preferably of from 0.6 to 1.1 $g/cm^3$. The mobilizer preferably has a low molecular weight, with the average molecular weight generally being in order of from 100 to 10,000 grams/mole, most preferably from 100 to 5,000 grams/mole.

As representative examples of suitable mobilizers, there may be mentioned hydrocarbon oils, halogenated hydrocarbon oils, phthalic ester oils, vegetable oils, silicone oils, low molecular weight noncrystalline polymer greases, such as hydrocarbon polymer greases, low molecular weight polyester greases, polyarylether greases, etc. It is to be understood that the above examples are only illustrative and the use of other mobilizers should be apparent to those skilled in the art from the teachings herein. The preferred mobilizer is a liquid which is not highly viscous, most preferably, a hydrocarbon oil or phthalic ester oil. Particularly preferred mobilizing oils are aliphatic hydrocarbon oils.

A second radiation stabilizer incorporated into the composition of the invention is a conventional hindered amine, preferably a hindered piperidine. Preferred hindered piperidines are 2,2,4,4-tetramethyl piperidine derivatives. The most preferred hindered amine stabilizer is a hindered bis(4-piperidinyl)-diester of a dicarboxylic acid. Representative examples of bis(hindered piperidinyl)diesters acceptable for use in the present invention, but not limited thereby, are the following: bis(2,2,6,6-tetramethyl-4-piperidinyl)-sebacate; the N,N'-dimethyl derivative thereof; bis(1,2,2,6,6-pentamethyl-4-piperidinyl)-2-n-butyl-2-(3,5-di-tertbutyl-4-hydroxybenzyl)malonate; and bis(1,2,2,6,6-pentamethyl-4-piperidinyl)sebacate. These hindered piperidines are commonly referred to as Tinuvin 770, Tinuvin 765, Tinuvin 144, and Tinuvin 292, respectively, and are available from the Ciba-Geigy Corporation.

The mobilizing additive may be incorporated into the polymer in a mobilizing amounts generally about 0.1 to 50, preferably about 1 to 20% by weight. For the hindered amine stabilizer, about 0.01 to 5.0, preferably about 0.05 to 3.0% by weight may be used.

The radiation stable lubricating additive of the invention may be an erucic acid derivative, such as erucyl alcohol or erucyl erucate. Preferred lubricating additives are amides of erucic acid such as erucamide or substituted erucamides having an alkyl group on the nitrogen. The most preferred radiation stable lubricant is erucyl erucamide.

The erucic acid derivative may be included in the composition at a concentration of about 0.1 to 2.0, preferably 0.2 to 0 6 most preferably about 0.3% by weight. The erucyl lubricants of the invention are commercially available from the Humko Chemical Division of Witco Chemical Co., Memphis, Tenn., or are synthesized from erucic acid by conventional means.

Other additives as known in the art may be added to provide other desirable properties to the composition. For example, fillers, coloring agents, antistatic materials, wetting agents and the like may be added in suitable quantities. Preferred compositions include a clarifier, preferably a dibenzylidene sorbitol clarifier, such as those described by Hamada et al., Mahaffey et al. or Williams et al. supra. Clarifying properties are conferred when the additive is formulated into the polyolefin composition in a quantity within the range of about 0.005 to 2.0% by weight. Higher percentages of additives may be used but generally provide no perceived advantage. The preferred concentration range may be from about 0.05 to 0.5%, most preferably, from about 0.1% to 0.3%.

Preparation of the composition of the invention from its constituent parts is routine and may be carried out by any conventional mixing means. Generally, polyolefin pellets and the additives are thoroughly mixed by stirring or tumbling, the mixture melted and the melt pelletized and molded or extruded into the shape of the desired article. As representative nonlimiting medical articles which may be fabricated from the composition of the invention, catheters, tissue culture flasks, and package films may be mentioned. Preferred articles have components in a slidable relationship wherein at least one of the components is fabricated from the composition of the invention. Thus, preferred articles are tube assemblies and syringes, most preferably two-piece syringes in which at least the syringe barrel is molded from the composition of the invention. It is, of course, evident that the composition may also be used to make nonmedical articles.

Sterilization of the composition or article of the invention is effected by exposure to a sterilizing amount of high energy radiation, for example, electron beam irradiation and particularly gamma irradiation from a cobalt-60 source. A sterilizing amount generally comprises from about 0.5 to 10 megarads, a typical dose being in a range of from about 1.0 to 5.0 megarads and usually from about 1.5 to 3.5 megarads. It is understood that higher doses could be employed but are generally not necessary.

It has been found that, after radiation sterilizing the composition of the invention by the procedure of Example VI, the sterilized or irradiated polymer is not embrittled, and moreover, does not develop any substantial embrittlement on aging; i.e., the polymer retains its flexibility. Thus, for example, prior to irradiation, such polymers have a bending angle of at least 90°, and in accordance with the present invention, the irradiated polymer subsequent to irradiation still has a bending angle of about 90°. Even after storage for a long period of time, the resistance to embrittlement of the irradiated polymer of the invention does not substantially diminish.

Clarity of a polyolefin composition is conventionally reported as the haze value. Haze values of the compositions of the invention may be determined in accordance with ASTM procedure D 1003 on the 0.040 in. step plaque of Example I. The haze value of composition C of Example I was about 59%. The haze value of composition C of Example I additionally containing about 0.1% of dibenzylidene sorbitol was 19%.

The COF of the composition of the invention may be determined by the method of Example V A, preferably after 48 hours, during which time the lubricant migrates to the surface of the composition to give a lubricious surface for which the lubricity is substantially stable over time. Friction between the barrel and plunger of the preferred two piece syringe of the invention may be determined by the procedure of Example VB.

The invention will be further described with respect to the following examples; however, the scope of the claims is not to be limited thereby.

EXAMPLE I

A radiation stable base composition was prepared from narrow molecular weight distribution polypropylene pellets having a ratio of weight average to number average molecular weight of 2.8; 4.7 parts by weight of aliphatic hydrocarbon oil and 0.0012 parts by weight of Tinuvin 770. Compositions A-C below were prepared by adding the following additives, in parts by weight, to the base composition:

| A | .003 parts oleamide |
|---|---|
| B | .003 parts erucamide |
| C | .003 parts erucyl erucamide |

The compositions were tumbled to give uniformly coated pellets, the coated pellets were melted, pelletized and injection molded into step plaques 50×75 mm in overall dimension having upper and lower steps of 0.080 and 0.040 in. thick respectively.

The plaques were set aside for 48 hours in order to allow and equilibrated amount of the lubricant to migrate to the surface. The COF was measured on the smooth side of the plaque by the sled test of Example VA. The samples were then irradiated with ca. 3 mrads from a cobalt 60 source and COF measurements taken about one hour after irradiation. It is seen from FIG. 1 that the COF prior to irradiation is about the same regardless of the lubricant used, and that after irradiation, the COF is higher. However, a much smaller increase in COF on irradiation is seen in compositions B and C lubricated with the erucyl derivatives of the invention compared to the composition A lubricated with the industry standard oleamide.

COMPARATIVE EXAMPLE II

Compositions were prepared from the base composition of Example I containing the following known lubricants. The compositions were injection molded into step plaques and tested for COF by the procedure of Example V A.
(1) N,N'-ethylene his stearamide
(2) N,N'-ethylene bis oleamide
(3) behenamide
(4) arachidamide
(5) oleyl alcohol
(6) polyoxyethylene(23) lauryl ether
(7) poly(vinyl stearate)
(8) glycerol monostearate
(9) N,N-ethylene bis octoylamide
(10) N,N-dipropyl-1,12, dodecyl diamide
(11) N,N-dihexadecyl dodecyl bisamide
(12) oleyl palmitamide
(13) stearyl erucamide
(14) stearyl alcohol After irradiation with 3 mrads, the compositions containing the above lubricants showed increases in COF substantially equal to or greater than that of the oleamide lubricated composition (IA) which itself was inferior to the erucyl amide lubricated compositions of the invention, as demonstrated by Example I and FIG. 1.

EXAMPLE III

The melted coated pellets of the compositions of Examples IA,B and C and the base composition of Example I were injection molded into syringe barrels adapted for use with a conventional polyethylene plunger. The friction between the plunger and the syringe barrel was determined by the procedure of Example VB one month after sterilization with different doses of cobalt 60 radiation.

Figure 2:
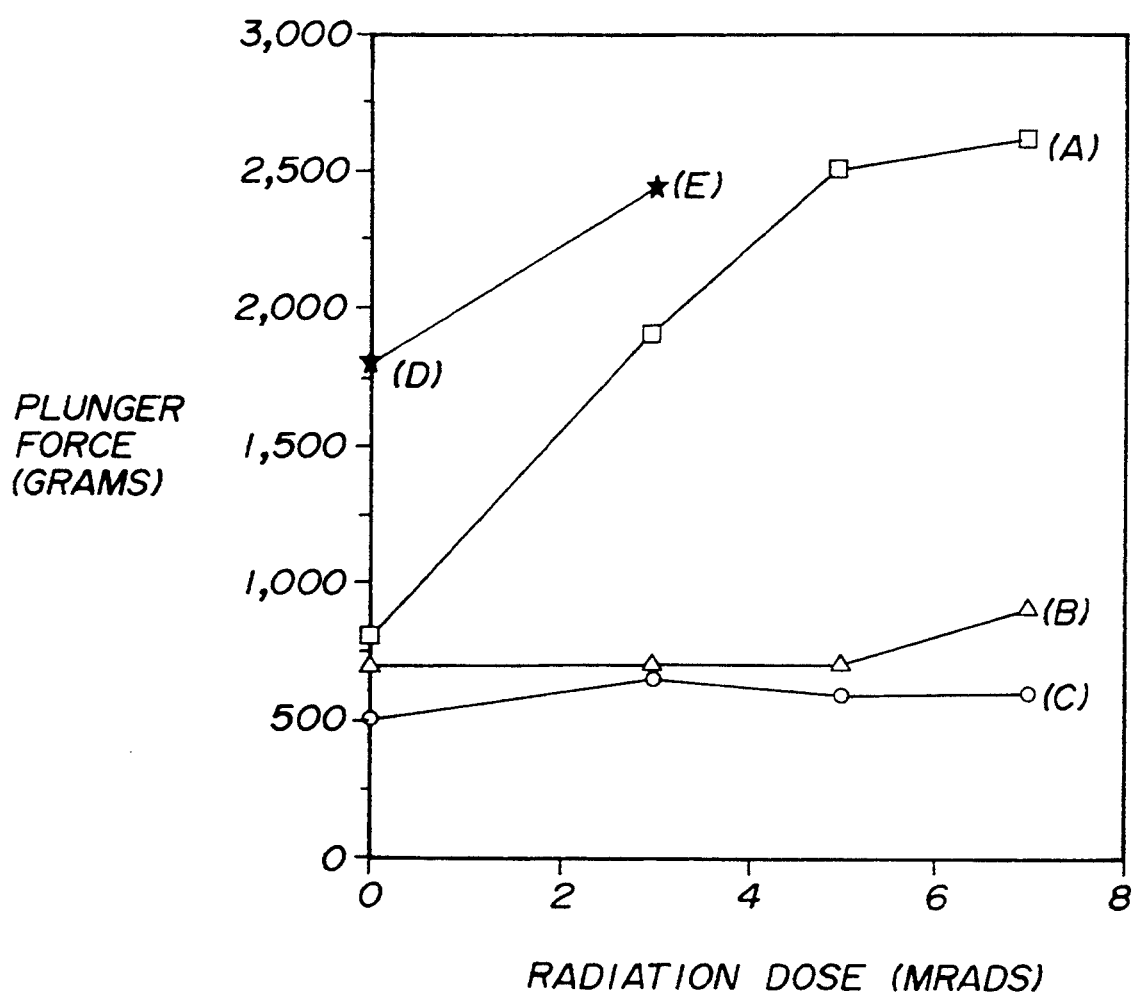
FIG. 2 compares the effect of radiation dosage on the friction between a polyethylene syringe plunger and syringe barrels molded from the compositions of FIG. 1.

The results of this experiment are given in FIG. 2. The nonlubricated base composition required a force of 1,800 g prior to irradiation (D) and 2,400 g after irradiation with 3 mrads (E). The force required for the erucamide (B) and erucyl erucamide (C) lubricated two-piece syringes is seen to be substantially lower and independent of radiation intensity up to 7 mrads. The force required for the oleamide lubricated composition (A) is seen to be higher than (B) and (C) at all radiation intensities and, after 3 mrads, requires about the same force as the nonlubricated and nonirradiated base composition (D). This result shows the lubricating property of oleamide to be severely compromised by radiation.

EXAMPLE IV

Long Term Lubricity Study

Figure 3:
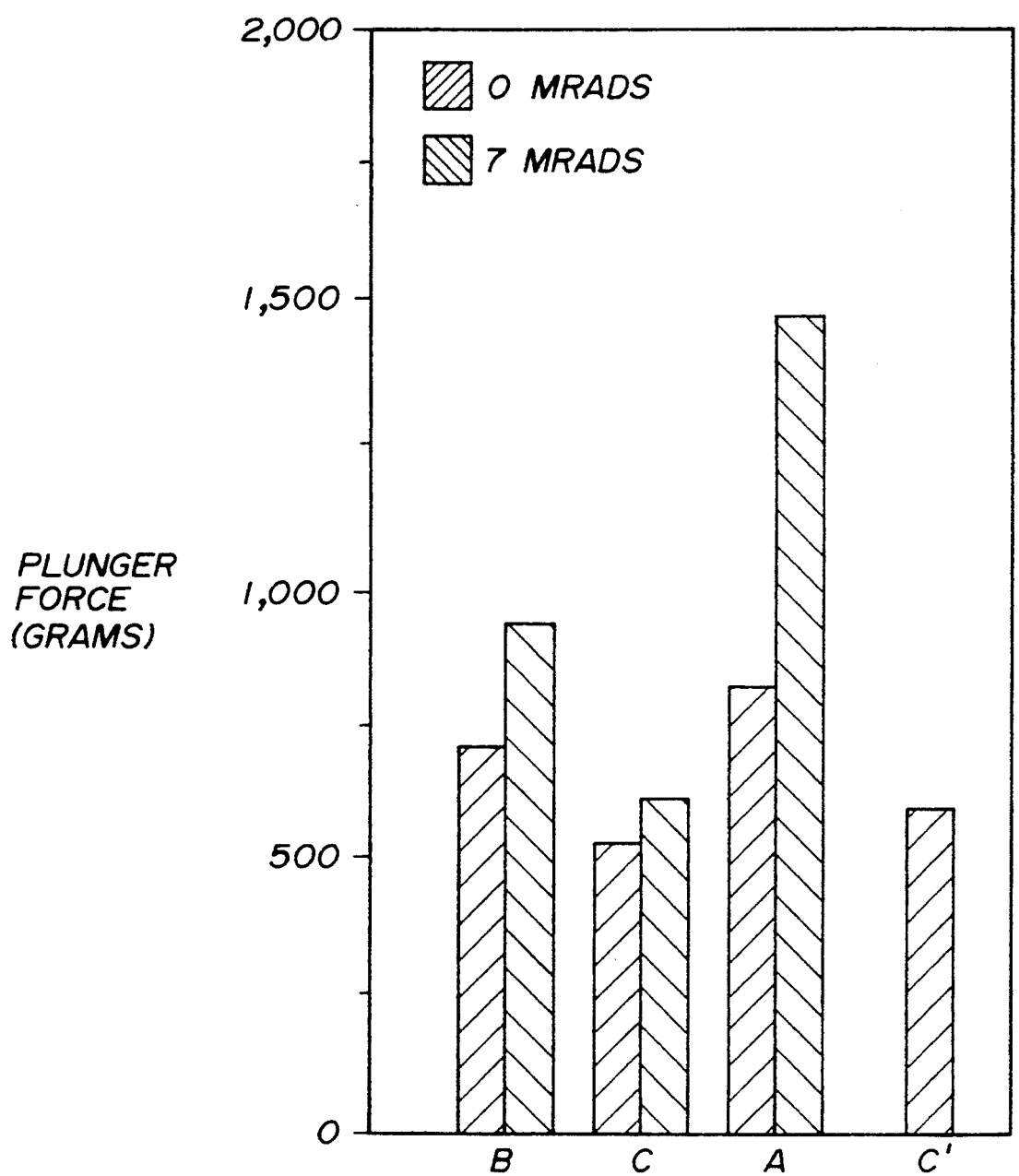
FIG. 3 compares the effect of a 7 mrad radiation dose on the friction between the plunger and syringe barrels of FIG. 2 after six months.

The syringe barrels from Example III which had been irradiated with 7 mrads were set aside at ambient conditions for a six month post irradiation study on retention of lubricity. The friction between the plunger and the syringe was determined by the procedure of Example VB. The results of this experiment are illustrated in FIG. 3. For comparison, the friction between the plunger and the barrel from composition IC after sterilization with the conventional commercial sterilant ethylene oxide is given in C'.

It is seen from FIG. 3 that, after six months under conditions which simulate shelf time, the friction of the erucamide (B) and erucyl erucamide (C) lubricated syringes is much lower than that of the oleamide lubricated syringe (A), and that the friction of the erucyl erucamide lubricated syringe is about the same six months after irradiation sterilization (C) as it is after ethylene oxide sterilization (C').

EXAMPLE V

Determination of Friction

A. Sled Test for Coefficient of Friction

A modification of the procedure described in ASTM D-1894 was used. A 25 mm polyethylene disc was affixed in a recess in the sled. The step plaque of Example I was secured onto a holding fixture and the lower side of the disc was placed in sliding contact with the smooth surface of the plaque. A 500 g weight was placed on the upper surface of the sled. The sled was connected by a steel wire to the load cell on the crosshead of the Universal Instron Testing Machine Model 1122 and pulled at constant speed so that the disc slid across the plaque while the average force required was recorded by the Instron.

B. Plunger Force Test for Friction in Syringe

A polyethylene syringe plunger was placed in the syringe barrel of Example III. The barrel was held stationary and the plunger was attached to the load cell on the movable crosshead of the Instron. The force in grams required to push the plunger into the barrel at constant speed was measured with the load cell.

EXAMPLE VI

Syringe Barrel Flange Bending for Determination of Embrittlement

Three cc polypropylene syringe barrels were molded from the composition of the invention and irradiated at 0.5 megarad/hour to a total dose of 0,2,3,5 and 7 megarad. Immediately after irradiation, and after storage away from direct sunlight for 3,6,9 and 12 months, the barrel flanges were tested for embrittlement. A minimum of two barrels (4 flanges) were tested for each radiation dose and for each time interval. The testing equipment was an Instron Tensile Tester, Model 1122, load cell 0–50 kg capacity equipped with standard Instron accessories, a microprocessor and a flange bending device. The barrel flange was secured in the Instron holder with the barrel 1 mm from the anvil face. The Instron was calibrated to traverse 90° at a test speed of 83 cm/min at a chart speed of 100 cm/min. The flange was bent through 90° followed by rotation and bending of the other flange through 90° while observing for breakage of the flange due to embrittlement.

What is claimed is:

1. A method for sterilizing a flexible shaped article having a lubricious surface while retaining the surface lubricity of the article comprising subjecting to a sterilizing amount of high energy radiation a flexible, shaped article comprising a composition including a polyolefin having a crystalline content of about 20 to 90 percent and a weight distribution wherein the ratio of the weight average molecular weight to the number average molecular weight is no greater than 6, a mobilizing amount of a liquid mobilizer compatible with said polyolefin having a density of about 0.6 to 1.9 grams per cubic centimeter, a radiation stabilizing amount of a hindered piperidine stabilizer, a clarifying amount of a dibenzylidene sorbitol clarifier, and a lubricating amount of erucylerucamide to produce a sterilized article which retains its flexibility.

2. The method of claim 1 wherein said sterilizing amount of radiation is about 0.5 to 10 megarads.

3. The method of claim 1 wherein said radiation is from a cobalt-60 source.

* * * * *